United States Patent [19]

Bottaro et al.

[11] Patent Number: 5,648,273

[45] Date of Patent: Jul. 15, 1997

[54] HEPATIC GROWTH FACTOR RECEPTOR IS THE MET PROTO-ONCOGENE

[75] Inventors: Donald P. Bottaro, Kensington; Jeffery S. Rubin, Rockville; Donna Faletto, Frederick; Andrew M.-L. Chan, Rockville, all of Md.; George F. Vande Woude, Berryville; Stuart A. Aaronson, Great Falls, both of Va.

[73] Assignee: The United States of America, as represented by the Department of Health and Human Services, Washington, D.C.

[21] Appl. No.: 642,971

[22] Filed: Jan. 18, 1991

Related U.S. Application Data

[63] Continuation-in-part of Ser. No. 457,556, Dec. 27, 1989, abandoned, and Ser. No. 582,063, Sep. 14, 1990, abandoned.

[51] Int. Cl.$^6$ .................................................. G01N 33/566
[52] U.S. Cl. ...................... 436/501; 435/7.23; 435/7.8; 436/503
[58] Field of Search .................................. 436/501, 503, 436/504; 435/7.23, 7.8

[56] References Cited

U.S. PATENT DOCUMENTS 5,030,565   7/1991   Niman et al. .................. 435/70.21

OTHER PUBLICATIONS

Miyazawa et al (1989) Biochem Biophys Res Comm 163:967–973.

Nakamura et al (1989) Nature 342:440–443.

Miyazawa et al (1989) "Molecular Cloning & Sequencing ——" Biochem Biophys Res Com 163:967–973.

Giordano et al (1989) "Tyrosine Kinase Receptor ——" Nature 339:155–156.

A. Volver in (E.T. Maggio Ed), *Enzyme–Immunoassay*, CRC Press Inc., 1980. Chapter 9, pp. 181–196.

Primary Examiner—David Saunders
Attorney, Agent, or Firm—Foley & Lardner

[57] ABSTRACT

The present invention relates to a complex comprising hepatocyte growth factor (HGF) and met proto-oncogene protein. The present invention also relates to methods for detecting the presence of HGF ligand, met proto-oncogene receptor and methods for isolating either the ligand or receptor or complex comprising both. The present invention further relates to methods of diagnostic proliferative disorders and diseases such as hepatitis or hepatocarcinogenesis by detecting these ligand-receptor pairs.

2 Claims, 3 Drawing Sheets

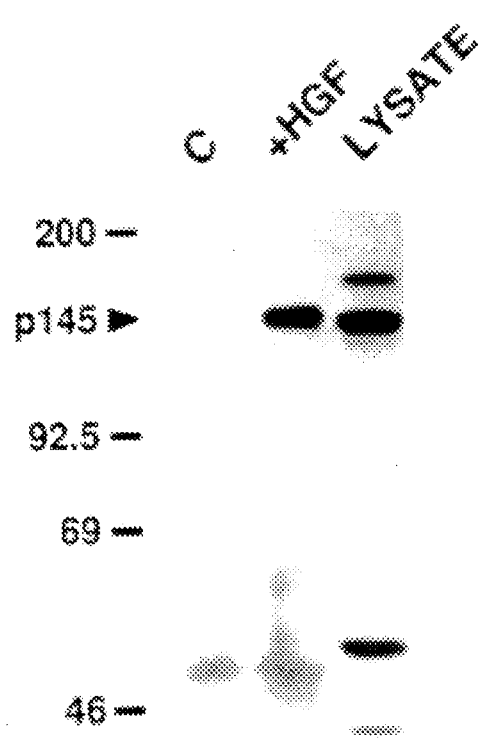
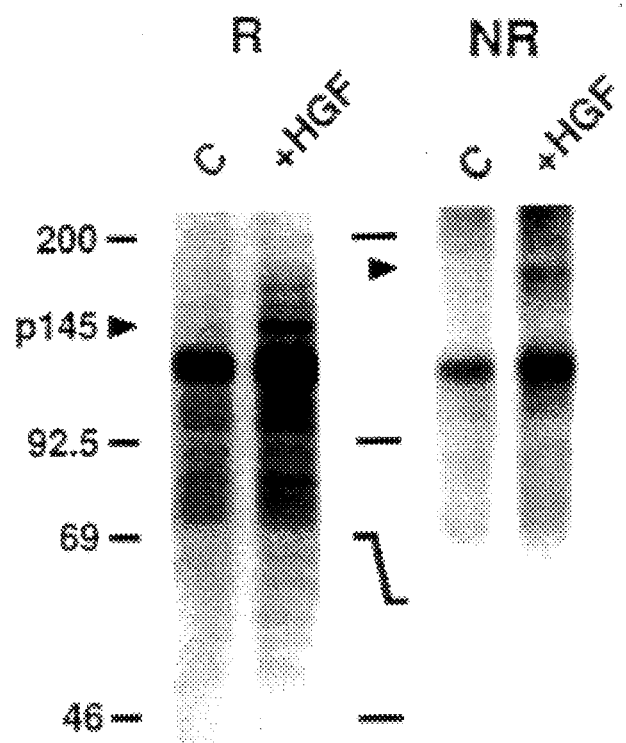

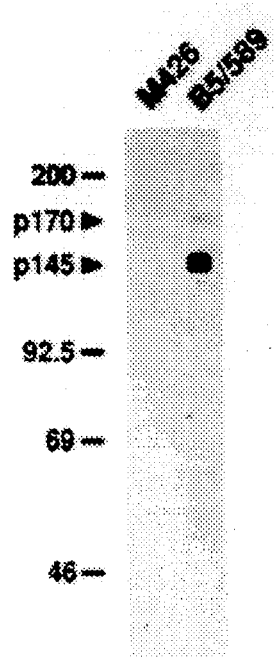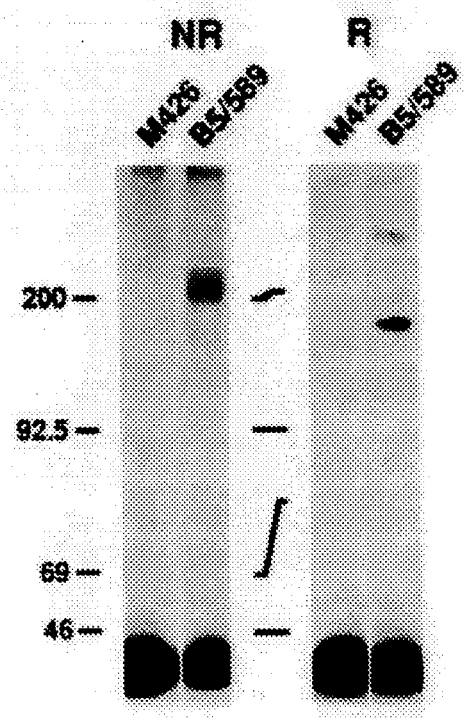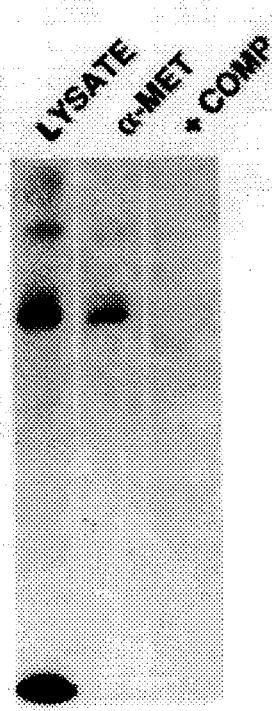

HEPATIC GROWTH FACTOR RECEPTOR IS THE MET PROTO-ONCOGENE

This is a continuation-in-part of application Ser. No. 07/457,566 filed Dec. 27, 1989 and now abandoned and application Ser. No. 07/582,063 filed Sep. 14, 1990 and now abandoned. The entire contents of both applications are hereby incorporated by reference.

FIELD OF THE INVENTION

The present invention relates to a complex comprising hepatocyte growth factor (HGF) and met proto-oncogene protein. The present invention also relates to methods for detecting the presence of HGF ligand, met proto-oncogene receptor and methods for isolating either the ligand, receptor or complex comprising both.

The present invention further relates to methods of diagnosing and treating conditions proliferative disorders such as hepatitis, hepatocarcinogenesis, carcinogenesis and wound healing. In particular, the present methods involve detection of the ligand-receptor pairs.

BACKGROUND OF THE INVENTION

Hepatocyte growth factor (HGF) was first purified from human and rabbit plasma and rat platelets on the basis of its ability to stimulate mitogenesis of rat hepatocytes (E. Gohoda et al., *J. Clin. Invest.* 81, 414 (1988); R. Zarnegar and G. Michalopoulos, *Cancer Res.* 49, 3314 (1989); T. Nakamura et al. *FEBS Lett.* 224, 311 (1987)). Thus, HGF may act as a humoral factor promoting liver regeneration after partial hepatectomy or liver injury (G. K. Michalopoulos, *FASEB J.* 4, 176 (1990)). The same factor was purified from human fibroblast culture medium and shown to act on melanocytes and a variety of epithelial and endothelial cells (J. S. Rubin et al., *Proc. Natl. Acad. Sci. U.S.A.* 88, 415 (1990)). Together with evidence of HGF expression in several organs (J. S. Rubin et al., *Proc. Natl. Acad. Sci. U.S.A.* 88, 415 (1990); K. Tashiro et al. *Proc. Natl. Acad. Sci. U.S.A.* 87, 3200 (1990); R. Zarnegar et al., *Proc. Natl. Acad. Sci. U.S.A.* 87, 1252 (1990); T. Kinoshita et al. *Biochem. Biophys. Res. Comm.* 165, 1229 (1989)), these findings indicate that HGF may also act as a paracrine mediator of proliferation for a broad spectrum of cell types. Molecular cloning of HGF revealed a remarkable structural homology to plasminogen and related serine proteases (J. S. Rubin et al., *Proc. Natl. Acad. Sci. U.S.A.* 88, 415 (1990); T. Nakamura et al., *Nature* 342, 440 (1989); K. Miyazawa et al., Biophys. Res. Comm. 163, 967 (1989)). Recent evidence that HGF induces rapid tyrosine phosphorylation of proteins in intact target cells suggests that a tyrosine kinase receptor might mediate its mitogenic signal (J. S. Rubin et al., *Proc. Natl. Acad. Sci. U.S.A.* 88,415 (1990)).

HGF is structurally related to the family of serine proteases that includes plasminogen, prothrombin, urokinase, and tissue plasminogen activator (J. S. Rubin et al., *Proc. Natl. Acad. Sci. U.S.A.* 88, 415 (1990)); T. Nakamura et al., *Nature* 342, 440 (1989)). As defined in the present invention, HGF includes a variant of HGF previously characterized as a broad-spectrum mitogen called plasminogen like growth factor (PLGF). Several proteases, including members of the serine protease family, stimulate DNA synthesis presumably through a proteolytic mechanism similar to tryptic activation of the insulin receptor (S. E. Shoelson et al. *J. Biol. Chem.* 263, 4852 (1988)). Only urokinase has been found to associate with a specific cell-surface receptor, which itself bears no homology to any known tyrosine kinase receptors (A. L. Roldan et al., *EMBO J.* 9, 467 (1990)).

It is clear that a need exists to identify the receptor of HGF. The present invention describes the complex comprising HGF and met proto-oncogene protein and identifies the met proto-oncogene as the receptor for HGF. The met proto-oncogene protein is a member of the tyrosine kinase growth factor receptor family. Knowledge of this receptor/ligand relationship should facilitate the study of proliferative disorders in which expression of these molecules may play an important role. Additionally, identification of the met proto-oncogene receptor HGF complex provides a means for identifying tissues other than liver tissue affected by factor binding.

SUMMARY OF THE INVENTION

It is an object of the present invention to provide a complex comprising a hepatocyte growth factor (HGF) ligand and met proto-oncogene protein receptor and methods of utilizing the complex.

Various other objects and advantages of the present invention will become apparent from the drawings and the following description of the invention.

In one embodiment, the present invention relates to a complex of a HGF ligand and met proto-oncogene receptor protein wherein said complex is free of protein with which it is naturally associated.

In another embodiment, the present invention relates to a complex comprising a HGF ligand and met proto-oncogene receptor protein wherein one member of said complex is bound to a solid support.

In yet another embodiment, the present invention relates to a method of detecting a HGF:met proto-oncogene receptor protein complex in a sample comprising reacting said sample with an antibody that binds specifically with either HGF or met proto-oncogene receptor protein on the complex. A positive immunological reaction is indicative of the presence of the complex in the sample.

In a further embodiment, the present invention relates to a method of diagnosing a proliferative disorder in a patient suspected of having the disorder comprising reacting a biological sample from the patient with an antibody that binds with a HGF-met proto-oncogene receptor protein complex.

In yet another embodiment, the present invention relates to a method of diagnosing a tissue undergoing regeneration in a patient comprising, reacting a biological sample from the patient with an antibody that binds to a HGF-met proto-oncogene receptor protein complex.

A further embodiment of the present invention relates to a method of diagnosing a diseased state in a patient suspected of having the stated disease comprising reacting a biological sample from the patient with an antibody that binds with a HGF- met proto-oncogene receptor protein complex.

In another embodiment, the present invention relates to a method for detecting HGF in a sample comprising contacting the sample with met proto-oncogene receptor protein under conditions such that binding of HGF present in the sample to the receptor is effected and detecting the presence of bound HGF.

In a further embodiment, the present invention relates to a method for detecting met proto-oncogene receptor protein in a sample comprising the steps of contacting the sample with HGF under conditions such that binding of said receptor present in the sample to HGF is effected and detecting the presence of bound receptor.

Another embodiment of the present invention relates to a diagnostic kits for measuring would healing and proliferative disorders. One type of kit comprises labeled HGF in one container and ancillary reagents suitable for use in detecting the presence or absence of met proto-oncogene receptor in a biological sample.

A second type of kit comprises labeled met proto-oncogene receptor protein in one container and ancillary reagents suitable for use in detecting the presence or absence of HGF in a biological sample.

The entire contents of all publications mentioned herein are incorporated by reference.

BRIEF DESCRIPTION OF THE DRAWINGS

FIG. 1 shows the tyrosine phosphorylation of p145 in B5/589 human mammary epithelial cells in response to HGF.

FIG. 2 shows the identification of p145 as the β-subunit of the c-met proto-oncogene product. FIG. 2a: Anti c-met immunoblot of anti-pTyr immunoprecipitates from control (C) and HGF-treated B5/589 cells. Samples for immunoprecipitation (2 mg protein) were prepared as described in FIG. 1a, resolved by 7.5% SDS-PAGE, transferred to Immobilon (Millipore) membranes and detected with monoclonal anti-c-met and [$^{125}$I]-protein-A. To quantify the percentage of c-met protein that was immunoprecipitable with anti-pTyr, 200 μg of B5/589 cell lysate (LYSATE) was resolved by SDS-PAGE and immunoblotted directly with monoclonal antibody to c-met. FIG. 2b: Autoradiogram of $^{32}$P-labeled phosphoproteins from control (C) and HGF-treated B5/589 cells resolved by 7.5% SDS-PAGE under reduced (R) and non-reduced (NR) conditions. Serum-starved cells were metabolically labeled with $^{32}$P-orthophosphate, left untreated (C) or treated with HGF, and immunoprecipitated with anti-pTyr as described in FIG. 1b. Samples were reduced with 100 mM β-mercaptoethanol before electrophoresis as indicated.

FIG. 3 demonstrates the covalent affinity cross-linking of $^{125}$I-labeled HGFp28 to the c-met protein-tyrosine kinase. FIG. 3a Immunoblot of lysates (200 μg protein) prepared from M426 human lung fibroblasts and B5/589 cells using monoclonal antibody to the cytoplasmic domain of c-met protein. FIG. 3b: Cross-linking of $^{125}$I-labeled HGFp28 to M426 and B5/589 cells resolved by 6.5% SDS-PAGE under non-reduced (NR) and reduced (R) conditions. HGFp28 was purified as described and radiolabeled with [$^{125}$I]-Na by the chloramine-T method (W. M. Hunter and F. C. Greenwood, Nature 194, 495 (1962)). Cells were incubated with HEPES binding buffer (D. P. Bottaro et al., J. Biol. Chem. 265, 12767 (1990) containing $^{125}$I labeled HGFp28 (5×10$^5$ cpm) for 45 min at 25° C., washed with cold HEPES-buffered saline (pH 7.4), and treated with disuccinimidyl suberate (D. P. Bottaro et al., J. Chem. 265, 12767 (1990). The cells were then solubilized with SDS and boiled for 3 min in the presence 100 mM β-mercaptoethanol as indicated. $^{125}$I-labeled proteins were resolved by 6.5% SDS-PAGE and autoradiography at −70° C.

FIG. 3c: Immunoprecipitation of [$^{125}$I]-HGFp28-cross-linked complexes from B5/589 cells with c-met peptide antiserum (A. Gonzatti-Haces et al., Proc. Natl. Acad. Sci. U.S.A. 85, 21 (1988)). Sample preparation and crosslinking prior to immunoprecipitation, performed as described in FIG. 3b, yielded the electrophoretic pattern shown in the left lane (LYSATE) under reduced conditions. The adjacent lanes show immunoprecipitation of the cross-linked species with c-met peptide antiserum (1:100) in the absence (α-MET) or presence (+COMP) of competing peptide (10 μg/ml). Immunoprecipitated proteins were absorbed to immobilized protein-G (Genex) and eluted with SDS prior to electrophoresis and autoradiography as described in FIG. 3b.

DETAILED DESCRIPTION OF THE INVENTION

Figure 1A:
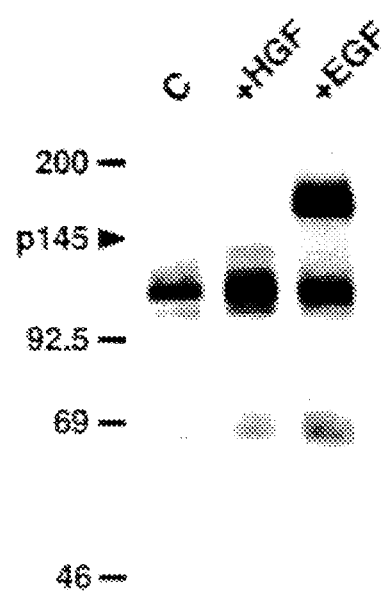
FIG. 1a: Immunoblot of phosphotyrosyl proteins from untreated control cells (C), cells treated with HGF, and with EGF (Collaborative Research). HGF was purified as described (J. S. Rubin et al., Proc. Natl. Acad. Sci. U.S.A. 88, 415 1990)). Serum-starved cells were exposed to growth factor (100 ng/ml) for 10 min at 37° C. as indicated, detergent-solubilized on ice, and immunoprecipitated with monoclonal anti-pTyr (Upstate Biotechnology). Immunoprecipitated proteins were resolved by 7.5% SDS polyacrylamide gel electrophoresis (SDS-PAGE) (U. K. Laemmli Nature 227, 680 (1970)), and immunoblotted with the same antibody as described (D. P. Bottaro et al.,J. Biol. Chem. 265, 12767 (1990)).

The present invention relates to a complex comprising hepatocyte growth factor (HGF) and met proto-oncogene protein. The present invention further relates to methods of utilizing the complex.

One embodiment of the present invention relates to a complex formed by the interaction of HGF with its receptor, the met proto-oncogene protein. The complex is free of protein with which it is naturally associated. The binding of HGF to its receptor, the met-proto-oncogene protein, regulates the intrinsic tyrosine kinase activity of the receptor.

The direct interaction of HGF with the c-met receptor tyrosine kinase suggests a biochemical mechanism of mitogenic signal transduction similar to that of insulin, EGF and other peptide growth factors. This interaction represents a significant functional divergence from HGF's structurally related family of serine protease homologs.

The present invention also relates to detection and quantitation methods that may be used in diagnostics to identify HGF (ligand), met-proto-oncogene receptor or the ligand-receptor complex. Since the met-proto-oncogene receptor is expressed on many cell types and tissues including the liver, the methods described herein provide a means for identifying tissues other than liver affected by HGF binding. The methods of the present invention also aid in understanding the role of the interaction between receptor and ligand in regulating biochemical and physiological mechanisms in a broad spectrum of tissues.

The present invention further relates to a method of detecting and quantitating HGF receptor in a biological sample using labeled HGF as a probe. Suitable labels include, for example, radiolabels such as $^{125}$I, and flourescein.

Using standard methodologies well known in the art, a biological sample can be extracted with a non-ionic detergent and incubated with labeled HGF in the presence or absence of unlabeled HGF. The resulting complex can be separated from the uncomplexed (or unbound) labeled material, for example, by immunoprecipitating the complex with a specific polyclonal or monoclonal antibody that recognizes the met-proto-oncogene receptor protein or the HGF-met proto oncogene receptor complex. The overall signal resulting from the presence of label associated with the resulting complex is compared with the signal from a mock sample. The mock sample is prepared using purified met-oncogene receptor protein in a known quantity treated the same way as the biological sample.

Alternatively, the complex may be separated from uncomplexed material by precipitating with polyethylene glycol. In both methodologies, the amount of label that is immunoprecipitated or precipitated is directly related to the amount of complex in the biological sample.

The present invention also relates to a method for detecting and quantitating HGF in a biological sample using labeled HGF receptor as a probe. The method is carried out as a reciprocal binding assay following the methodology described above except substituting as antibody, one that specifically recognizes HGF or the HGF-met proto-oncogene receptor complex.

The present invention also relates to further methods of detecting and quantitating HGF-met proto-oncogene receptor complexes in a sample. In one aspect, complexes are detected and quantitated using antibodies. Antibodies utilized in this embodiment can be directed against HGF, met-proto-oncogene receptor protein or the HGF-receptor complex. Antibodies can be either polyclonal or monoclonal. A sample can be extracted with non-ionic detergent and incubated with labeled HGF or met-proto-oncogene receptor protein. After incubation, the sample is covalently cross-linked with a bifunctional reagent such as a chemical cross-linker, for example, disuccinimidil suberate (DSS). After quenching the reaction with a quenching agent, the sample is immunoprecipitated with specific antibody or precipitated with polyethylene glycol. Quantitation requires chromatographic separation by, for example, gel electrophoresis, followed by autoradiography.

In another method for detecting HGF-met proto-oncogene receptor complexes in a sample, the simultaneous expression of HGF and met proto-oncogene receptor mRNAs are determined. Simultaneous co-expression of HGF and met proto-oncogene receptor can be determined by Northern analysis using oligo- or cDNA probes derived from the sequence of either gene to identify mRNA or using the polymerase chain reaction (PCR) or any combination. Northern analysis and the PCR technology are methods well known to those skilled in the art.

The present invention further relates to diagnostic methodologies using the methods described above. The disorders which diagnosed by the methods of the present invention include, for example, proliferative disorders such as hepatocellular carcinoma or other carcinomas of tissues that normally express met proto-oncogene receptor. Such tissues can be derived from epithelial cells such as skin, lung, stomach, kidney or colon, liver or endothelial cells, such as those contained in the vascular lining or bone marrow, or hematopoietic stem cells. The present diagnostic methods can also be used to measure wound repair in tissues derived from the cells described above, and in cells that normally express HGF such as platelets, fibroblasts (stromal tissue of skin and other organs) and spleen.

Inactivation of the HGF/met mitogenic pathway provides the basis for therapeutic methodologies designed to diminish or arrest normal or pathological cell proliferation. These methodologies include the production of genetically engineered HGF species that lack or possess an impaired met-binding domain, or that lack or possess an impaired activating domain, but that otherwise retain the structural and biochemical characteristics of HGF. Similarly, production of genetically engineered met species that lack or possess an impaired HGF-binding domain, or lack or possess an impaired tyrosine kinase domain, but which otherwise retain the structural and biochemical characteristics of the met protein. These methodologies also include the production of a water-soluble form of met protein consisting of the extracellular HGF-binding domain that can act as an antagonist of normal met protein activation by HGF. The delivery of the genetically engineered HGF or met protein species described above to the selected site of action may be achieved using conventional methods of drug delivery, gene transfer, or any combination thereof.

Artificial activation of the HGF/met mitogenic pathway provides the basis for therapeutic methodologies designed to restore, replace, or enhance naturally occurring wound repair mechanisms. These methodologies include application to the wound site of genetically engineered HGF or met species that enhance the binding interaction between met and HGF and thereby create an artificially sustained HGF/met interaction. For example, site-directed mutagenesis of the HGF-binding domain of met, or the met-binding domain of HGF (or both) may be used to create a member of the HGF/met pair with higher binding affinity for the other member of the pair and thus affect accelerated growth or regeneration of the wounded tissue. Similarly, conventional recombinant DNA techniques could be used to enhance or sustain the kinase activity of the met protein normally regulated by HGF binding, including met mutations possessing a constitutively activated tyrosine kinase. The delivery of the genetically engineered HGF or met protein species described above to the selected site of action can be achieved using conventional methods of drug delivery, gene transfer, or any combination thereof. Activation of the HGF/met mitogenic pathway by means of supplementing the natural expression of met by recombinant DNA techniques in combination with exogenously administered HGF is also included.

EXAMPLES

Example 1

Figure 1B:
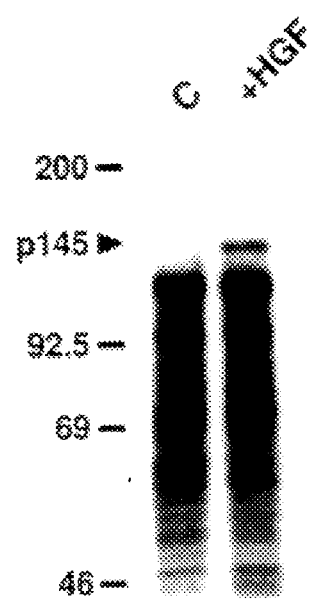
FIG. 1b: An autoradiogram of $^{32}$p-labeled phosphoproteins from control (C) and HGF-treated cells. Serum-starved cells were metabolically labeled with $^{32}$P-orthophosphate (1.0 mCi/ml) as described (M. F. White and C. R. Kahn, in Insulin Receptors, Part A: Methods for the Study of Structure and Function, C. R. Kahn and L. Harrison, Eds. (Liss, 1988) pp. 125–147). The cells were treated with HGF (100 ng/ml) for 10 min at 37° C. as indicated, and detergent-solubilized on ice. Phosphotyrosyl proteins were immunoprecipitated with anti-pTyr and resolved by 7.5% SDS-PAGE.
Figure 1C:
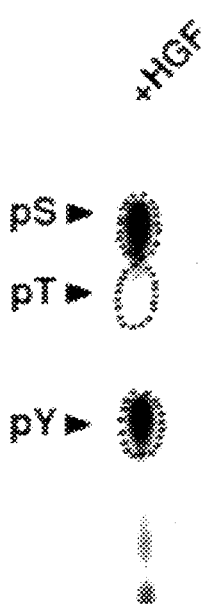
FIG. 1c: Phosphoamino acid analysis of p145 from lane 2 of FIG. 1b: was performed as described (M. F. White and C. R. Kahn, Insulin Receptors, Part A: Methods for the Study of Structure and Function, C. R. Kahn and L. Harrison, Eds. Liss, 1988, pp. 125–147). The dotted circles indicate the migration of unlabeled phosphoserine (pS), phosphothreonine (pT), and phosphotyrosine (pY).

Tyrosine Phosphorylation of p145 in B5/589 Human Mammary Epithelial Cells in Response to HGF The human mammary epithelial cell line B5/589 is particularly sensitive to the mitogenic effects of HGF (J. S. Rubin et al., Proc. Natl. Acad. Sci. U.S.A. 88, 415 (1990)). Intact serum-starved B5/589 cells were treated with HGF (approximately 100 ng/ml) for 10 min at 37° C. and solubilized on ice. Phosphotyrosyl proteins were isolated from cell lysates by immunoprecipitation with antibody to phosphotyrosine (anti-pTyr). These proteins were resolved by SDS polyacrylamide gel electrophoresis (SDS-PAGE) and immunoblotted with the same antibody. Several phosphotyrosyl proteins were detected in untreated cells by this method (FIG. 1a). Treatment of intact cells with HGF induced phosphorylation of a 145-kD protein (p145) (FIG. 1a, center lane). B5/589 cells exposed to epidermal growth factor (EFG) displayed tyrosine phosphorylation of the EGF receptor, but not p145 (FIG. 1a, right lane). When lysates from control and HGF-treated cells that had been labeled with $^{32}$P-orthophosphate were used for immunoprecipitation with anti-pTyr, phosphorylation of p145 was specifically detected in HGF-treated cells (FIG. 1b). Phosphoamino acid analysis of $^{32}$P-labeled p145 confirmed the presence of phosphotyrosine, and revealed the presence of phosphoserine as well (FIG. 1c). The HGF-stimulated phosphorylation of p145 on tyrosine and its apparent molecular weight were consistent with the possibility that p145 represented the receptor tyrosine kinase for HGF.

Example 2

Identification of p145 as the β Subunit of the c-met Proto Oncogene Product

A number of receptor-like molecules have been described for which there are as yet no known ligands. One of these is the c-met proto oncogene product, which is a receptor-like tyrosine kinase comprised of disulfide-linked subunits of 50-kD (α) and 145-kD (β) (P. R. Tempest et al. Br. J. Cancer 58, 3 (1988); S. Giordano et al., Oncogene 4, 1383 (1989)). In the fully processed c-met product, the α subunit is extracellular, and the βsubunit has extracellular, transmembrane, and tyrosine kinase domains as well as sites of tyrosine phosphorylation (S. Giordano et al., Oncogene 4, 1383 (1989); A. A. Gonzatti-Haces et al., Proc. Natl. Acad. Sci. U.S.A. 85, 21 (1988).

To test the hypothesis that p145 might represent the c-met protein β subunit, proteins immunoprecipitated by anti-pTyr from control and HGF-treated B5/589 cells were immunoblotted with a monoclonal antibody directed against the cytoplasmic domain of the c-met product. Specifically, a mouse monoclonal IgG raised against recombinant human c-met protein cytoplasmic domain was used. Recognition of human c-met protein by immunoprecipitation or immunoblotting can be specifically blocked by incubating in the presence of the recombinant protein fragment.

The prominent 145-kD protein observed specifically in HGF-treated cells (FIG. 2a) provided direct evidence that this mitogen induced phosphorylation of the c-met protein on tyrosine residues. When whole lysates prepared from identically treated cells were blotted directly with the c-met antibody, the percentage of c-met protein phosphorylated on tyrosine in response to HGF could be quantitated (FIG. 2a). It is estimated that at least 10% of the total cellular c-met protein content was immunoprecipitated by anti-pTyr after HGF stimulation. Analysis of the time course of HGF action revealed that the c-met protein could be recovered by immunoprecipitation with anti-pTyr within 1 min of treatment and that this effect persisted for at least 3 hours. Comparison of the electrophoretic mobility of p145 under reduced and non-reduced conditions confirmed that it was the β subunit of the c-met protein (FIG. 2c). Without reduction, the 50-kD α subunit of the c-met protein remains disulfide-linked to the β subunit and substantially retards its migration in SDS-PAGE (P. R. Tempest et al., Br. J. Cancer 58, 3 (1988); S. Giordano et al., Oncogene 4, 1383 (1989); P. R. Tempest et al., FEBS Lett 209, 357 (1986); M. Park et al., Proc. Natl. Acad. Sci. U.S.A. 84, 6379 (1987); A. Gonzatti-Haces et al., Proc. Natl. Acad. Sci. U.S.A. 85, 21 (1988)). Similarly, p145 immunoprecipitated from $^{32}$P-labeled B5/589 cells that had been treated with HGF displayed a shift in mobility characteristic of the c-met proto oncogene product when subjected to reduced or non-reduced electrophoretic conditions (FIG. 2c). Together these results identified p145 as the c-met protein β subunit and established that HGF stimulated its phosphorylation on tyrosine residues.

Example 3

$^{125}$I-HGFp28 is Physically Associated with the c-met Protein-Tyrosine Kinase The rapidity and extent of c-met protein tyrosine phosphorylation in response to HGF supported the possibility that c-met protein was the cell-surface receptor for HGF. However, there is evidence that receptor kinases can phosphorylate other receptors (D. F. Stern and M. P. Kamps, EMBO J. 7, 995 (1988); C. R. King et al.,EMBO J. 7, 1647 (1988)). Thus, conclusive identification of the c-met product as the HGF receptor required a demonstration of their direct interaction. $^{125}$I-labeled HGF was unsuitable for covalent affinity cross-linking because it consisted of a mixture of single chain and heterodimeric labeled species. A smaller form of HGF with similar binding properties, designated HGFp28, was $^{125}$I-labeled as a single entity and used to characterize the HGF receptor.

HGFp28 was labeled with [$^{125}$I]Na by the chloramine-T method as follows: HGFp28 (3 μg in 50 μl of 20 mM phosphate buffer containing 1.0M NaCl, pH 7.4) was reacted with chloramine-T (1.2 μg in 4 μl of phosphate buffer) and [$^{125}$I]Na (1 μCi) at 24° C. for 1 min. The reaction was terminated by addition of sodium metabisulfite (10 μg in 8 μl of phosphate buffer). The mixture was diluted with phosphate buffer containing 0.1% bovine serum albumin (200 μl) and applied to a column (300 μl packed volume) of heparin-Sepharose CL-6B that had been equilibrated in phosphate-buffered saline containing 0.1% BSA (PBS/BSA). The column was washed with 30 ml of PBS/BSA and eluted with PBS/BSA containing 1.0M NaCl (200 μl/fraction), removing 98% of trichloroacetic acid-precipitable radioactivity from the column. Peak fractions (specific activity: 150 to 250 μCi/μg) were 99% trichloroacetic acid-precipitable, and migrated as a single band on SDS-PAGE.

Comparative cross-linking studies were performed using $^{125}$I-labeled HGF p28 on B5/589 cells and M426 human fibroblasts, an HGF-insensitive cell line which also lacks detectable amounts of c-met protein (FIG. 3a). The $^{125}$I-labeled HGFp28 cross-linked to its receptor on B5/589 cells migrated as a 210-kD protein complex under non-reduced conditions (FIG. 3b). Under reduced conditions, a major 170-kD complex was observed (FIG. 3b). These apparent molecular sizes were consistent with a direct interaction between the labeled HGFp28 and the 145-kD β subunit of the c-met protein. Under reduced conditions, two minor bands of 190-kD and about 300-kD were also detected (FIG. 3b). Cross-linking of $^{125}$ I-labeled HGFp28 to the species observed under reduced conditions was blocked by addition of either unlabeled HGFp28 or HGF-neutralizing antisera. Under identical conditions, $^{125}$I-labeled HGFp28 failed to cross-link to any large proteins in M426 cells (FIG. 3b).

To establish that $^{125}$I-labeled HGFp28 was physically associated with the c-met protein, labeled HGFp28 cross-linked complexes were immunoprecipitated with a polyclonal antiserum (A. Gonzatti-Haces et al., Proc. Natl. Acad. Sci. U.S.A. 85, 21 (1988) specific to the carboxyl-terminal 28 amino acids of the β subunit of the c-met protein. The covalently cross-linked major 170-kD and minor 300-kD species detected under reduced conditions were immunoprecipitated by the antibody, and their detection was specifically blocked by competing peptide (FIG. 3c). These results demonstrate a direct molecular interaction between $^{125}$I-labeled HGFp28 and the c-met β subunit. The composition of the minor 300-kD cross-linked species remains to be determined. All of these findings establish that the c-met product is the cell surface receptor for HGF.

While the foregoing invention has been described in some detail for purposes of clarity and understanding, it will be appreciated by one skilled in the art from a reading of this disclosure that various changes in form and detail can be made without departing from the true scope of the invention.

What is claimed is:

1. A method for detecting HGF in sample comprising the steps of:
   (i) contacting said sample with met proto-oncogene receptor protein under conditions such that binding of HGF present in said sample to said receptor is effected and
   (ii) detecting the presence of bound HGF.

2. A method for detecting met proto-oncogene receptor protein in a sample comprising the steps of:
   (i) contacting said sample with HGF under conditions such that binding of said receptor present in said sample to HGF is effected and
   (ii) detecting the presence of bound receptor.

* * * * *